United States Patent [19]

Dambreville et al.

[11] Patent Number: 5,797,913
[45] Date of Patent: Aug. 25, 1998

[54] DEVICE FOR SECURING BONE PARTS AFTER OSTEOTOMY, OR FOR REDUCING A BONE FRACTURE AND SECURING THE FRACTURED BONE PARTS, ONCE THESE PARTS HAVE BEEN BROUGHT TOGETHER

[75] Inventors: Alain Dambreville, Quimper; Patrick Pfaifer, Lyons, both of France

[73] Assignee: Groupe Lepine, Lyons, France

[21] Appl. No.: 797,331

[22] Filed: Feb. 10, 1997

[30] Foreign Application Priority Data

Jul. 28, 1995 [FR] France ................ 95 09441

[51] Int. Cl.⁶ .................................. A61B 17/56
[52] U.S. Cl. .................... 606/72; 606/103; 606/151
[58] Field of Search .................... 606/60, 62, 72, 606/75, 103, 104, 105, 151, 87; 411/485, 515

[56] References Cited

U.S. PATENT DOCUMENTS 3,959,960  6/1976  Santos.
5,478,353  12/1995  Yoon ........................ 606/151

FOREIGN PATENT DOCUMENTS 2221111  10/1974  France.
824377   12/1951  Germany.
1916924  6/1965  Germany.
2125556  6/1972  Germany.
2519488  11/1976  Germany.

*Primary Examiner*—Michael Powell Buiz
*Assistant Examiner*—Julian W. Woo
*Attorney, Agent, or Firm*—Oliff & Berridge, PLC

[57] ABSTRACT

According to the invention, this device comprises:
- a grapnel-shaped element (6) comprising a central rod (6a) which is semi-rigid, that is to say exhibits a relative flexibility perpendicular to its longitudinal axis, capable of passing through the bone parts (2, 2a) to be secured, this rod (6a) being continued at one end via at least two branches (6b) which are curved through substantially 180 degrees and whose free ends are sharp-pointed, and the rod comprising, at its other end, a ring (6c) for pulling the grapnel-shaped element (6) through the bone parts (2, 2a) to be secured;
- a lock washer (8), and
- a metal sleeve (9) capable of being engaged on the rod (6a), until it comes into abutment against the lock washer (8), and of being crimped on the rod (6a) after the bone parts to be secured have been brought together and the grapnel-shaped element (6) has been tensioned.

5 Claims, 2 Drawing Sheets

DEVICE FOR SECURING BONE PARTS AFTER OSTEOTOMY, OR FOR REDUCING A BONE FRACTURE AND SECURING THE FRACTURED BONE PARTS, ONCE THESE PARTS HAVE BEEN BROUGHT TOGETHER

The present invention relates to a device for securing bone parts after osteotomy, or for reducing a bone fracture and securing the fractured bone parts, once these parts have been brought together.

It also relates to an instrument designed for putting this device into place.

BACKGROUND OF THE INVENTION

It is well known to secure the parts of a bone on which an osteotomy has been performed, or to reduce a bone fracture and secure the fractured bone parts, by means of rigid components such as nails, screws or rigid plates, especially made of metal.

The osteotomy or the fracture is in some cases situated in proximity to a muscle attachment, in other words to the position on a bone subjected to considerable tensile stresses. The existing rigid devices are unsuitable for these particular indications, given that they can become detached from the bone under the action of these stresses.

The various components of the existing devices may not be able to be put into place in cases where the bone site is of small dimensions, for example in the case of osteotomy or fracture of the patella or of certain parts of articulations, such as the olecranon, the greater trochanter or the tibial plateau.

In addition, the positioning of these rigid components in relation to the bone may not be optimum, depending on the configuration of the site and the orientation of the osteotomy or of the fracture, thus making the operation difficult to perform.

In other cases, the fitting of these components could have harmful consequences, in particular occupying or damaging the site of osseous attachment of a tendon.

The present invention aims to overcome these various disadvantages by making available a device which can be implanted in any type of bone site, even in proximity to a muscle attachment, in the case of a site having small dimensions or an unusual configuration, irrespective of the orientation of the fracture, and without compromising the osseous attachment of a tendon which may be situated in proximity.

SUMMARY OF THE INVENTION

The device comprises:
- a grapnel-shaped element comprising a central rod which is semi-rigid, that is to say exhibits a relative flexibility perpendicular to its longitudinal axis, capable of passing through the bone parts to be secured, this rod being continued at one end via at least two branches which are curved through substantially 180 degrees and whose free ends are sharp-pointed, and the rod comprising, at its other end, a ring for pulling the grapnel-shaped element through the bone parts to be secured;
- a lock washer intended to be engaged on the rod after the latter has passed through the bone parts to be secured, and to come into abutment against one of these bone parts, and
- a metal sleeve capable of being engaged on the rod, until it comes into abutment against the lock washer, and of being crimped on the rod after the bone parts to be secured have been brought together and the grapnel-shaped element has been tensioned.

To put this device into place, a hole is first made in the bone parts, more or less perpendicular to their surfaces to be joined, and the grapnel-shaped element is then engaged in this hole until its end provided with the ring emerges on the opposite side from the side of introduction.

By pivoting the grapnel-shaped element about itself, the curved branches can be oriented in the most appropriate way, depending on the specific configuration of the bone site or the possible presence of a ligament attachment.

The lock washer and the sleeve are engaged on the end of the rod protruding from the bone, until the lock washer comes into abutment against the bone wall.

A pull is then exerted on the grapnel-shaped element in such a way as to insert the ends of the curved branches into the bone wall, and then to bring the bone parts gradually toward one another.

Once the bone parts have been brought together, the pulling is continued in order to press the bone parts against one another and to ensure the deep anchoring of the ends of the curved branches in the bone wall.

The sleeve is then crimped on the rod and the portion of the latter protruding beyond the sleeve is cut off.

This device has relatively small dimensions and can be used on any type of bone site, even of small dimensions. A set of several grapnel-shaped elements can be provided, each element having different lengths of rod and different lengths of curved branches adapted to the different types of osteotomy or fracture which may arise.

By virtue of the spacing of the ends of the curved branches, the grapnel-shaped element has a good seat in relation to the bone and is perfectly anchored.

The shape of this element, allied with the possibility of orienting the curved branches, permits adaptation of the anchoring to the particular configuration of the site or to the presence of a tendon in proximity to the anchoring zone.

The central rod for its part ensures a semi-rigid securing of the bone parts to be brought together, with tensioning of the grapnel-shaped element. This semi-rigidity has the effect that the device adapts to the relative natural elasticity of the bone and can be implanted in bone sites subject to tensile stresses. The tensioning of the grapnel-shaped element permits the knitting together of the bone parts under optimum conditions.

The implantation of this device does not require any screw passing through the bone walls and does not involve any damage to the site.

The central rod of the grapnel-shaped element is preferably made of stainless steel or titanium and has a diameter of the order of 1.2 millimeter, which gives it the appropriate semi-rigidity.

A flexible pulling thread is advantageously fastened to the ring of the grapnel-shaped element. This thread makes it easier to pull this element and to bring together the bone parts which are to be secured.

The instrument for putting the device into place has, for its part, a rigid body comprising a longitudinal bore with a diameter greater than the width of the ring of the central rod but smaller than that of the sleeve to be crimped, and a drum integral with rotational control means and situated to the rear of the bore and in communication with it.

Once the grapnel-shaped element has been engaged through the bone parts, the flexible pulling thread is introduced into the bore of the instrument and is then wound around the drum. The instrument is then engaged on that end of the grapnel-shaped element protruding from the bone, until it comes into abutment against the sleeve, and the drum is rotated so as to exert a pull on the thread, and thereby to bring the bone parts together and tension the device.

DETAILED DESCRIPTION

Figure 1:
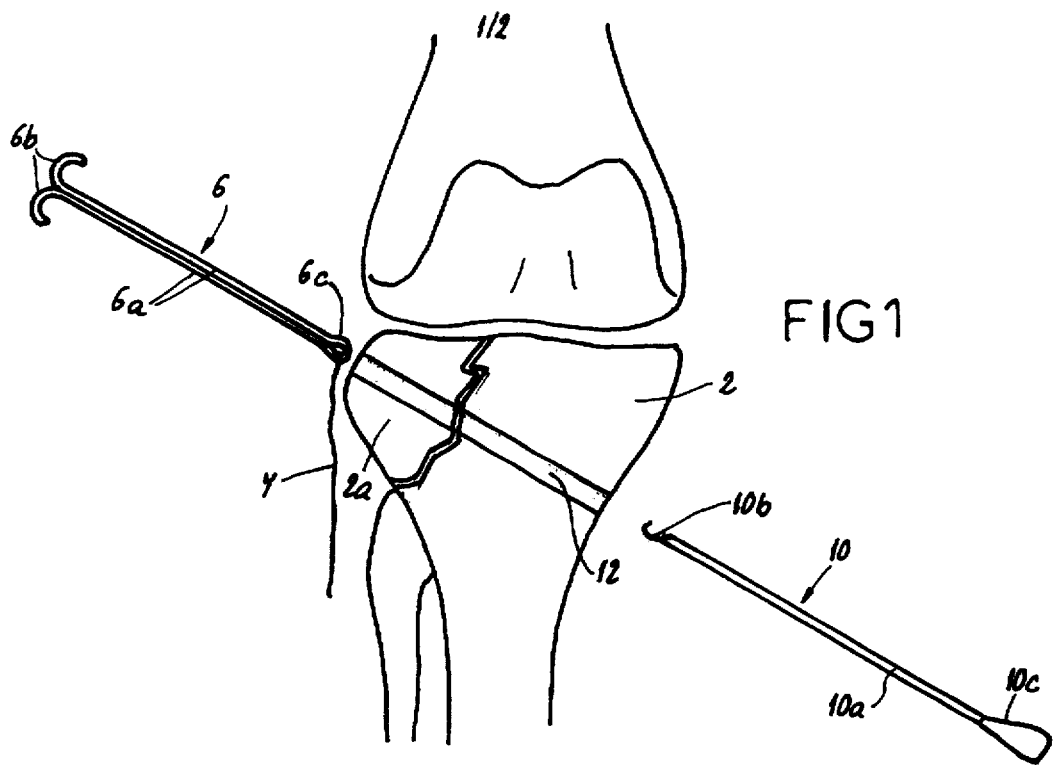
FIG. 1 is a front view thereof prior to implantation on a knee joint whose tibial plateau is fractured.

FIGS. 1 to 4 represent a knee joint, with a fracture of the tibial plateau 2, and a device for reducing this fracture and for securing the fractured parts 2, 2a once these have been brought together.

The device comprises a grapnel-shaped element 6 formed by appropriate bending of a metal rod, a lock washer 8, and a metal sleeve 9 capable of being crimped on the element 6.

The element 6 has a central rod 6a capable of passing through the bone parts 2, 2a. This rod 6a is made of stainless steel and has a diameter of 1.2 millimeter, so as to be semi-rigid, that is to say to exhibit a relative flexibility perpendicular to its longitudinal axis.

At one end the rod 6a is continued via two branches 6b which are curved through substantially 180 degrees and whose free ends are sharp-pointed. At its other end the rod 6a comprises a ring 6c for pulling the element 6 through the bone parts 2, 2a.

A flexible pulling thread 7 is fastened to the ring 6c.

Figure 2:
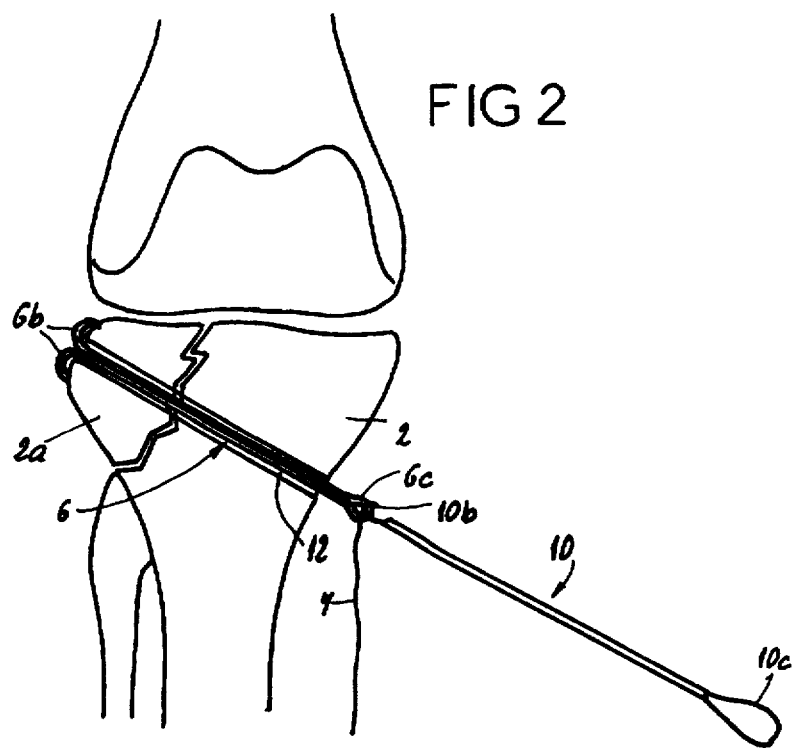
FIGS. 2 to 4 are views thereof similar to FIG. 1, during three successive phases of implantation.

FIGS. 1 and 2 also represent two instruments 10, 11 designed for putting the device into place.

The instrument 10 comprises an elongate body 10a capable of being engaged in the osseous hole 12 intended to receive the rod 6a. At one end this body 10a has a tab 10b which is curved in order to form a hook which can be engaged in the ring 6c. At its other end the body 10a is equipped with a hand grip 10c formed by a metal loop.

The instrument 11 has a rigid body 11a in which a recess 11b is formed and which is continued at one end via a gripping butt 11c. At its other end it comprises a longitudinal bore 13, with a diameter greater than the width of the ring 6c, but smaller than that of the sleeve 9, and opening into the recess 11b via a coaxial hole having a diameter greater than the diameter of the thread 7. Approximately where the body 11a joins the butt 11c, the instrument 11 also comprises a drum 14 which is integral with a key 15 for rotating it. This drum 14 is situated to the rear of and opposite a hole which is coaxial to the bore 13, has a diameter greater than the diameter of the thread 7, and also opens into the recess 11b.

After preparing the hole 12 in the bone parts 2, 2a, more or less perpendicular to the fracture, the instrument 10 is engaged in this hole 12 and then in the ring 6c.

The element 6 is then pulled into the hole 12 until its end provided with the ring 6c emerges from the bone on the side opposite the side of introduction.

The thread 7 is pulled all the way through the hole 12, as is shown in FIG. 2.

If appropriate, the element 6 can be pivoted about itself in such a way as to orient its curved branches 6b in the most suitable manner depending on the specific configuration of the bone site or the possible presence of a ligament attachment.

The washer 8 and the sleeve 9 are engaged on that end of the rod 6a protruding from the bone until the washer 8 comes into abutment against the bone wall, then the thread 7 is introduced into the bore 13 and into the holes following the latter and is wound around the drum 14.

The instrument 11 is then engaged on that end of the element 6 protruding from the bone, until it comes into abutment against the sleeve 9, and the drum 14 is rotated in such a way as to exert a pull on the thread 7, and thus on the rod 6a.

Figure 3:
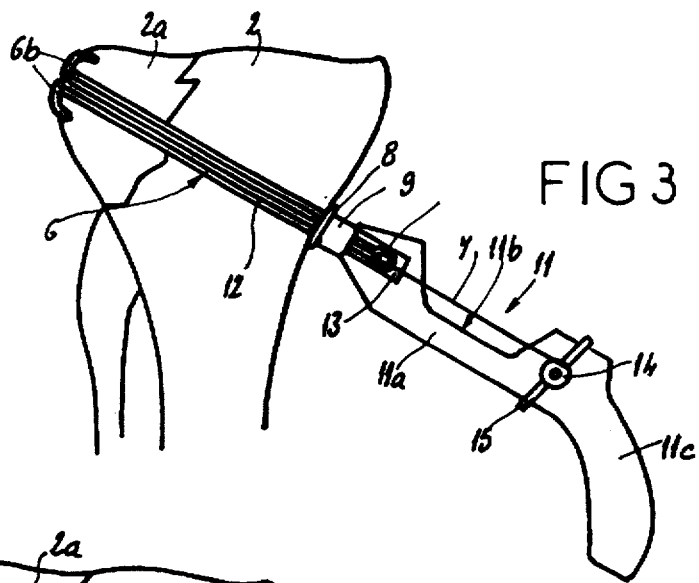

This pulling allows the ends of the curved branches 6b to be inserted in the bone wall and then the fractured bone parts 2, 2a to be brought gradually toward one another, as is shown in FIG. 3.

Once the bone parts 2, 2a have been brought together, the pulling is continued in order to press these bone parts 2, 2a one against the other and to ensure the deep anchoring of the ends of the curved branches 6b.

Figure 4:
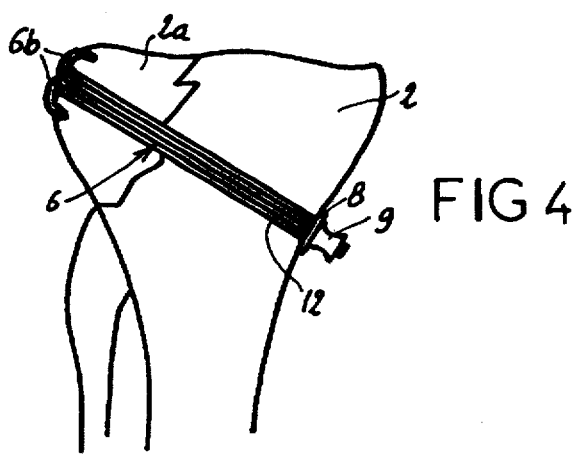

The sleeve 9 is then crimped on the rod 6a, and that portion of the rod 6a protruding beyond the sleeve 9 is then cut off, as is shown in FIG. 4.

The device has relatively small dimensions and can be used on any type of bone site, even of small dimensions.

Figure 5:
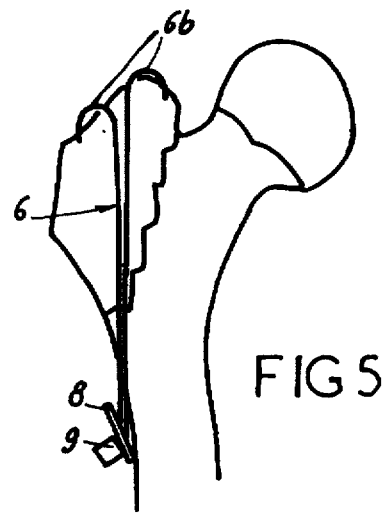
FIGS. 5 and 6 are simplified views of this device, after implantation on the end of a femur.
Figure 6:
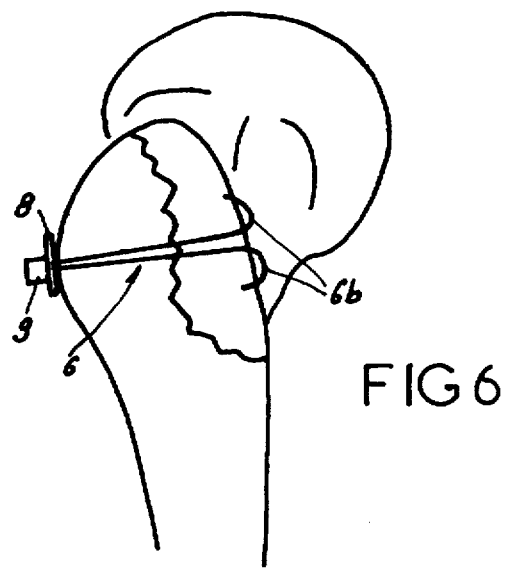

FIGS. 5 and 6 show the implantation of the device in the greater trochanter. The rod 6a can be bent at the point where its end protrudes from the bone, if this is necessary to hold the washer 8 in position.

The curved branches 6b have a relative flexibility allowing them to adapt to the particular configuration of the bone site, as FIG. 5 shows in the case of the greater trochanter, although this is an extreme case of deformation.

The device also proves very suitable in cases of fracture of the patella or fractures of certain parts of articulations, such as the olecranon.

A set of several elements 6 can be provided, each element having different lengths of rod 6a and different lengths of branches 6b adapted to the different types of fractures which may arise. For example, elements 6 having total lengths of 10, 15, 18, 20, 100 or 140 millimeters and, in the area of the curved branches 6b, widths of 15, 15, 18, 20, 15 or 15 millimeters, respectively, can be envisaged.

By virtue of the spacing of the ends of the curved branches 6b, the element 6 has a good seat in relation to the bone and is perfectly anchored.

The shape of this element 6, allied with the possibility of orienting the branches 6b, permits adaptation of the anchoring to the particular configuration of the site or to the presence of a tendon in proximity to the anchoring zone.

The central rod 6a for its part ensures a semi-rigid securing of the bone parts 2, 2a to be brought together, with tensioning, which permits adaptation of the device to the relative natural elasticity of the bone and permits the knitting together of these parts under optimum conditions.

In addition, the implantation of this device does not require any screw passing through the bone walls and does not involve any damage to the site.

What is claim is:

1. A device for securing bone parts after osteotomy, or for reducing a bone fracture and securing the fractured bone parts, once these parts have been brought together, comprising:

a grapnel-shaped element comprising a central rod having a longitudinal axis and a first and a second end, said central rod being semi-rigid, that is to say exhibiting a relative flexibility perpendicular to its longitudinal axis, comprising at least two branches at said first end, which are curved through substantially 180 degrees and whose free ends are sharp-pointed, and comprising a ring at said second end;

a lock washer intended to be engaged on said central rod, and a metal sleeve capable of being crimped, said metal sleeve being capable to be engaged on said central rod and to comes into abutment against the lock washer.

2. The device as claimed in claim 1, wherein said central rod is made of stainless steel or titanium and has a diameter of the order of 1.2 millimeter.

3. The device as claimed in claim 1, wherein a flexible pulling thread is fastened to said ring.

4. The device as claimed in claim 1, comprising a set of several grapnel-shaped elements, each element having different lengths of central rod and different lengths of curved branches adapted to the different types of fractures.

5. An instrument for putting into place the device as claimed in claim 3, having a rigid body comprising a longitudinal bore with a diameter greater than the width of said ring but smaller than that of said metal sleeve, and a drum integral with rotational control means for winding said pulling thread, said drum being and situated to the rear of the bore and in communication with it.

* * * * *